United States Patent [19]
Lind et al.

[11] Patent Number: 6,001,578
[45] Date of Patent: Dec. 14, 1999

[54] METHODS OF SCREENING FOR MODULATORS OF UNCOUPLING PROTEIN-2 (UCP-2) AS POTENTIAL TREATMENTS FOR OBESITY

[75] Inventors: Peter Lind, Uppsala; Erik Walum, Åkersberga, both of Sweden

[73] Assignee: Pharmacia & Upjohn AB, Stockholm, Sweden

[21] Appl. No.: 09/105,035

[22] Filed: Jun. 26, 1998

Related U.S. Application Data

[60] Provisional application No. 60/052,247, Jul. 11, 1997.

[30] Foreign Application Priority Data

Jun. 26, 1997 [SE] Sweden ................................ 9702457

[51] Int. Cl.$^6$ .............................. C12Q 1/68; C12Q 1/02; C12Q 1/00
[52] U.S. Cl. .................................... 435/6; 435/4; 435/29; 424/9.1
[58] Field of Search ....................... 435/4, 6, 29; 424/9.1

[56] References Cited

U.S. PATENT DOCUMENTS

| | | | |
|---|---|---|---|
| 5,807,740 | 9/1998 | Amaral et al. ........................... | 435/325 |
| 5,849,514 | 12/1998 | Amaral et al. ............................ | 435/29 |

FOREIGN PATENT DOCUMENTS

| | | |
|---|---|---|
| 2 733 513 | 10/1996 | France . |
| WO 96/16031 | 5/1996 | WIPO . |
| WO 98/12302 | 3/1998 | WIPO . |

OTHER PUBLICATIONS

Fleury et al., Nature Genetics 15(3):269–272 (1997).
Gimeno et al., Diabetes 46(5):900–906 (1997).
Vidal–Puig et al., Biochemical and Biophysical Research Communications 235(1):79–82 (1997).
Umekawa et al., European Journal of Endocrinology 136(4):429–437 (1997).
Savontaus et al., European Journal of Pharmacology 328(2–3):207–215 (1997).
*Webster's Ninth New Collegiate Dictionary.* Frederick C. Mish, Editor in Chief. Merriam–Webster Inc., Springfield, MA, 1990, p. 385.
Shimabukuro, M., et al, *Biochem.Biophys.Res. Comm* 237(2), 1997: 359–361.
Okuno, A., et al., *Diabetes Front* 8(4), 1997: 499–501. Abstract only.
*STN Chem Abstr.* 127(16): 215488, Ghorbani et al.
*STN Chem Abstr.* 127(8): 104191, Ghorbani et al.
*STN Chem Abstr.* 125(7): 76139, Nagase et al.
Zhou, Y–T., et al, *PNAS, USA 94*, Jun. 10, 1997: 6386–6390.

*Primary Examiner*—Johnny F. Railey, II
*Attorney, Agent, or Firm*—Pollock, Vande Sande & Amernick

[57] ABSTRACT

The invention relates to a method for treatment of obesity, metabolic syndrome and/or non-insulin dependent diabetes mellitus by administering a drug capable of modulating the regulation of UCP-2, the use of a drug capable of modulating the regulation of UCP-2 for the production of drug for treatment of obesity, metabolic syndrome and/or non-insulin dependent diabetes mellitus and pharmaceutical composition comprising a pharmaceutically effective amount of such a drug. The invention is also related to methods for screening for potential drugs against obesity, metabolic syndrome and/or non-insulin dependent diabetes mellitus and the use of cDNA probe for determination of upregulation of UCP-2 for potential drugs against obesity, metabolic syndrome and/or non-insulin dependent diabetes mellitus.

24 Claims, 5 Drawing Sheets

METHODS OF SCREENING FOR MODULATORS OF UNCOUPLING PROTEIN-2 (UCP-2) AS POTENTIAL TREATMENTS FOR OBESITY

RELATED APPLICATIONS

The present invention claims the benefit of co-pending provisional U.S. patent application Ser. No. 60/052,247, filed on Jul. 11, 1997.

FIELD OF THE INVENTION

The present invention relates to method for treatment of obesity, metabolic syndrome and/or non-insulin dependent diabetes mellitus by administering a drug capable of modulating the regulation of UCP-2. The present invention also relates to the use of a drug capable of modulating the regulation of UCP-2 for the production of a drug for treatment of obesity, metabolic syndrome and/or non-insulin dependent diabetes mellitus. The present invention also relates to method for screening for potential drugs against obesity, metabolic syndrome and/or non-insulin dependent diabetes mellitus comprising the measurement of UCP-2 activity by biochemical, chemical or physical methods.

BACKGROUND OF THE INVENTION

Obesity is a disease with strongly increasing prevalence, and has reached epidemic proportions in the industrialized world. This disease is essentially characterized by an unbalance between energy intake and expenditure, which, without interference, leads to an endless increase in adipose tissue mass and body weight.

Appetite and energy intake are influenced by several hormonal effectors and neurotransmitters acting in the peripheral as well as the central nervous system. Examples of neurotransmitters acting to increase appetite and, concomitantly, body weight, are neuropeptide Y, melanin concentrating hormone, galanin, as well as glucocorticoid hormones. Examples of hormones or neurotransmitters that counteract feeding and stimulate reduction in adipose mass are melanocortin, corticotropin releasing factor, as well as the recently described peptide hormone leptin.

Brown adipose tissue (BAT) is a well characterized tissue which is well developed in newborn mammals, including man. One important task of BAT is to generate heat and maintain body temperature homeostasis in newborns, as well as in small animals, e.g. rodents.

The uncoupling protein, UCP-1, occurs in mitochondria, and seems to be the most important protein for generating heat in BAT. It does so by burning calories using a pathway that allows dissipation of the proton electrochemical gradient across the inner mitochondrial membrane in BAT during fuel oxidation. The fuel oxidation process is uncoupled for oxidative phosphorylation of ADP to ATP, thus generating heat which is distributed from BAT to the rest of the body via the circulation. The physiological external stimulus for uncoupling activity in BAT is cold temperature. This will increase the sympathetic nervous system activity and release of catecholamines leading to stimulation of beta3 adrenoreceptors present on the surface of brown adipocytes.

Recently, a new protein denoted UCP-2 has been discovered, which is expressed not only in BAT, but also in white adipose tissue (WAT), skeletal muscle, lung, heart, placenta, etc. (Fleury C, et al. (1997) "Uncoupling protein-2: a novel gene linked to obesity and hyperinsulinemia" Nat Genet 15(3), 269–272; Gimeno, R E., et al., (1997) "Cloning and characterization of an uncoupling protein homolog: a potential molecular mediator of human thermogenesis" Diabetes 46(5), 900–906). The UCP-2 protein has a 59% identity to UCP-1, and is upregulated in WAT in mice in response to feeding. This is in contrast to UCP-1, which is physiologically upregulated by cold in mice.

International patent document WO 9616031, to The Upjohn Company, discloses aminoguanidine carboxylates, e.g. [1-(hydrazinoiminomethyl)hydrazino]acetic acid for the treatment of non-insulin dependent diabetes mellitus. The novel and claimed compounds reduce the abnormally elevated blood glucose level and have an increased glucose tolerance.

SUMMARY OF THE INVENTION

We have now found that a drug-induced upregulation of UCP-2 mRNA is possible. Furthermore, we have found that, as a consequence of this, the level of UCP-2 protein, mitochondrial activity, and heat flow all increase. This serves as a foundation of the invention related to the drug-induced increase of metabolic efficiency, increase in energy expenditure, and increase thermogenesis by genetic or transcriptional upregulation of UCP-2 in adipose tissue. Drugs that increase energy expenditure are useful in the treatment of obesity, non-insulin dependent diabetes, as well as the metabolic syndrome. Obesity can be caused by different reasons such as non-insulin dependent obesity, increase in triglycerides, increase in carbohydrate bound energy and low energy expenditure. An increase in energy expenditure includes the elevated utilization of both circulating and intracellular glucose and triglycerides, free or stored as glycogen or lipids as fuel for energy and/or heat production. The present invention relates to a method for treatment of obesity, metabolic syndrome and/or non-insulin dependent diabetes mellitus by administering a drug capable of modulating the regulation of UCP-2 mRNA, and thus an increase of metabolic efficiency, increase in energy expenditure, and increase thermogenesis by genetic or transcriptional upregulation of UCP-2 in adipose tissue. The present invention also relates to the use of a drug capable of modulating the regulation of UCP-2 mRNA for the production of drug for treatment of obesity, metabolic syndrome and/or non-insulin dependent diabetes mellitus and pharmaceutical composition comprising a pharmaceutically effective amount of such a drug. The invention is also related to methods for screening for potential drugs against obesity, metabolic syndrome and/or non-insulin dependent diabetes mellitus as defined in the claims and other aspects, also defined in the claims. The measurement of UCP-2 activity as upregulation of UCP-2 transcription/mRNA can be done by biochemical, chemical or physical methods, all well known for persons skilled in the art.

Screening with pharmacological or biochemical methods can e.g. be performed on mice by the use of candidate drugs or on cell-lines such as 3T3-L1 or 3T3-F442A, that optionally can be differentiated to adipocyte-like cells. The gene for UCP-2 and a reporter-gene (e.g. $E$ $coli$ $\beta$-galactosidase, chloramphenicol acetyltransferase, alkaline phosphatase or firefly luciferase) can also be used for the measurement of the UCP-2 activity.

The invention is illustrated with four examples, using an aminoguanidine carboxyloic acid, [1-(hydrazinoiminomethyl)hydrazino]acetic acid, (AG) as the substance capable of modulating the regulation of UCP-2. This is, however, no limitation of the invention in its broadest aspects.

DETAILED DESCRIPTION OF THE INVENTION

Definitions

| | |
|---|---|
| C5BL/6J ob/ob mice | Obese mice homozygous for a point mutation in the OB gene |
| SSPE | Sodium chloride (0.15 M), Sodium phosphate (10 mM), EDTA (1 mM), pH 7.4 |
| SDS | Sodium dodecylsulphate |
| AG | [1-(hydrazinoiminomethyl)hydrazino]acetic acid |

EXAMPLE 1
Upregulation of UCP-2

Six C57BL/6J ob/ob mice (Bomholtsgård, Denmark) were treated by peritoneal injection with either the compound AG (80 mg/kg) or saline (3 mice in each group). The mice were sacrified after 20 hours and intra-abdominal fat, and skeletal muscle samples were removed from each mouse. Total RNA was extracted from these samples using the guanidinium thiocyanate method essentially as described by Sambrook et al, (1989) "Molecular cloning: a laboratory manual", Cold Spring Harbor Laboratory Press, (2nd edition). The tissues were homogenized, together with 6 ml GTC (4M guanidinium thiocyanate, 25 mM Na-citrate, 8.06 mM 2-mercaptoethanol, final adjusted pH 7.0) in a Polytron homogenizer (Brinkmann) at high speed for 1–2 minutes. 300 ml, 10% sodium lauryl sarcosinate was added to a final concentration of 0.5%, then mixed thoroughly. This was centrifuged at 5000 g, 10 minutes at room temperature. The supernatant was transfered to a 50 ml Falcon tube and drawn six times through a 22-gauge needle. The tissue/GTC solution was layered on a 5.7 M cesium chloride solution (buffered by 8 mM sodium acetate and sterile filtered) and centrifuged at 32000 rpm in a swing-out SW41 rotor for 17 hours at room temperature. The pellets were dissolved in 2×200 ml diethylpyrocarbonate (DEPC) treated water and transfered to microcentrifuge tubes. One tenth of the volume of 3M sodium acetate and 2 volumes of 95% ethanol was then added, followed by precipitating the RNA in −20° C. for more than 30 minutes. The RNA was collected by centrifugation at 15000 g, 15 minutes at 4° C. The pellet was washed in 70% ethanol and centrifuged for 5 minutes at 15000 g. The supernatant was removed and the pellet was vacuum dried for 5 minutes. The RNA was resuspended in 100 ml DEPC-treated water and kept on ice. The integrity of the RNA was confirmed by separation on a 1% MP agarose (Boehringer Mannheim) gel. The RNA was then capillary blotted onto a GeneScreen Plus (DuPont NEN Research Products) membrane. The protocols used for the transfer and detection of the RNA are found in the technical manual: "GeneScreen and GeneScreen Plus; Hybridization Transfer—Membranes; Transfer and Detection Protocols", DuPont, NEN Research Products, 549 Albany St., Boston, Mass., USA.

The cDNA probe used for detecting UCP-2 was derived from the I.M.A.G.E. consortium clone No. 440295 and was amplified from the pT7T3D-Pac vector (Pharmacia&Upjohn) by PCR using the two primers 5'-CCAGTCACGACGTTGTAAA-3', SEQ ID NO. 1 and 5'-CACAGGAAACAGCTATGAC-3', SEQ ID NO. 2. The probe was purified from a low-melting agarose gel prior to $^{32}$P labelling which was carried out with the RediPrime DNA labelling kit kit (Amersham).

Figure 1A:
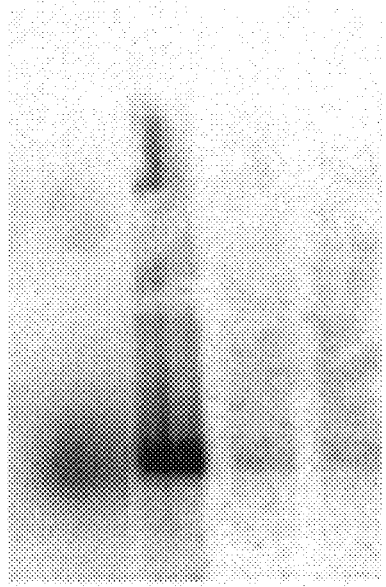
FIG. 1. Upper panel: RNA blotting filter hybridized to $^{32}$P-labelled human uncoupling protein-2 cDNA probe. Bottom panel:RNA blotting filter hybridized to $^{32}$P-labelled human β-actin cDNA probe.
Figure 1B:
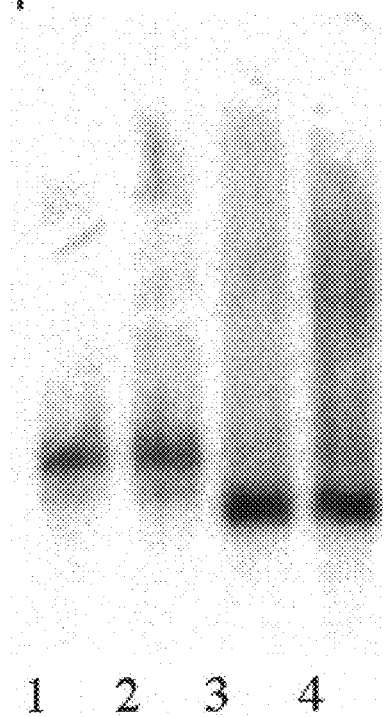

The RNA blotting filter was hybridized with the labelled probe in a 50% formamide solution at 42° C. overnight with subsequent high stringency washing using four 2×SSPE for 15 minutes at room temperature, followed by two 2×SSPE, 2% SDS for 45 minutes at 65° C. and, finally, two 15 minute washes in 0.1×SSPE at room temperature. After the final wash, filter bound radioactivity was detected and quantified using a PhosporImager (Molecular Dynamics, Inc.). The results are shown in FIG. 1. (top panel). After washing to remove filter-bound radioactivity, the RNA blotting filter was also hybridized to a $^{32}$P-labelled probe based on human β-actin cDNA to serve as a control for the mRNA content of each lane. The results are shown in FIG. 1. (bottom panel).

The relative expression levels of UCP-2 mRNA between samples of saline and AG treated mice, was calculated using the PhosphorImager radioactive counts detected within the bands corresponding to UCP-2 mRNA, and normalized against the radioactive counts within the bands corresponding to actin, the latter of which do not change significantly between saline and AG treated samples. The data (illustrated in FIG. 2.) indicate a 3.6-fold induction of UCP-2 mRNA in white adipose tissue after treatment with AG, and a 1.3 fold induction in skeletal muscle.

Figure Legends

FIG. 1. Top panel: RNA blotting filter hybridized to $^{32}$P-labelled human uncoupling protein-2 cDNA probe. Lane 1, white adipose tissue from saline treated mice; lane 2, white adipose tissue from AG treated mice; lane 4, skeletal muscle from saline treated mice; lane 4, skeletal muscle from AG treated mice. Bottom panel: RNA blotting filter hybridized to $^{32}$P-labelled human β-actin cDNA probe. Lane 1, white adipose tissue from saline treated mice; lane 2, white adipose tissue from AG treated mice; lane 4, skeletal muscle from saline treated mice; lane 4, skeletal muscle from AG treated mice.

Figure 2:
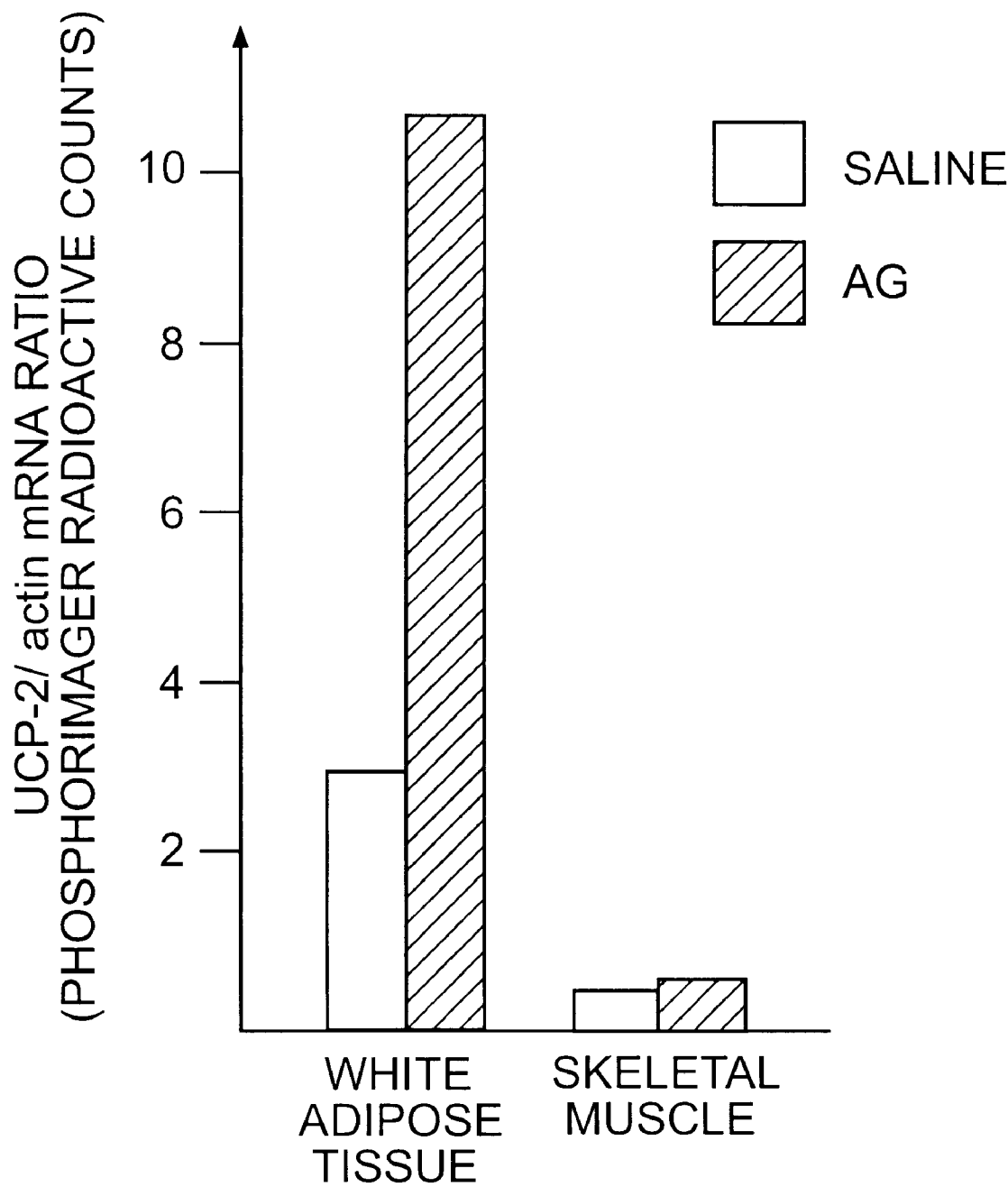
FIG. 2. Represents a graph illustrating regulation of UCP-2 mRNA levels in white adipose and skeletal muscle tissue by AG.

FIG. 2. Regulation of UCP-2 mRNA levels in white adipose and skeletal muscle tissue by AG. The white bars indicate saline treated control tissue, and the stippled bars indicate AG treated tissue. The UCP-2 mRNA levels were determined with a PhoshorImager (Molecular Dynamics) and are normalized against actin mRNA levels.

From these figures it is clearly seen that UCP-2 mRNA is strongly upregulated by AG in white adipose tissue compared to treatment with placebo (saline). This is in contrast to skeletal muscle where only a marginal change in UCP-2 mRNA levels could be seen.

EXAMPLE 2
Increase in Mitochondrial Activity

Figure 3:
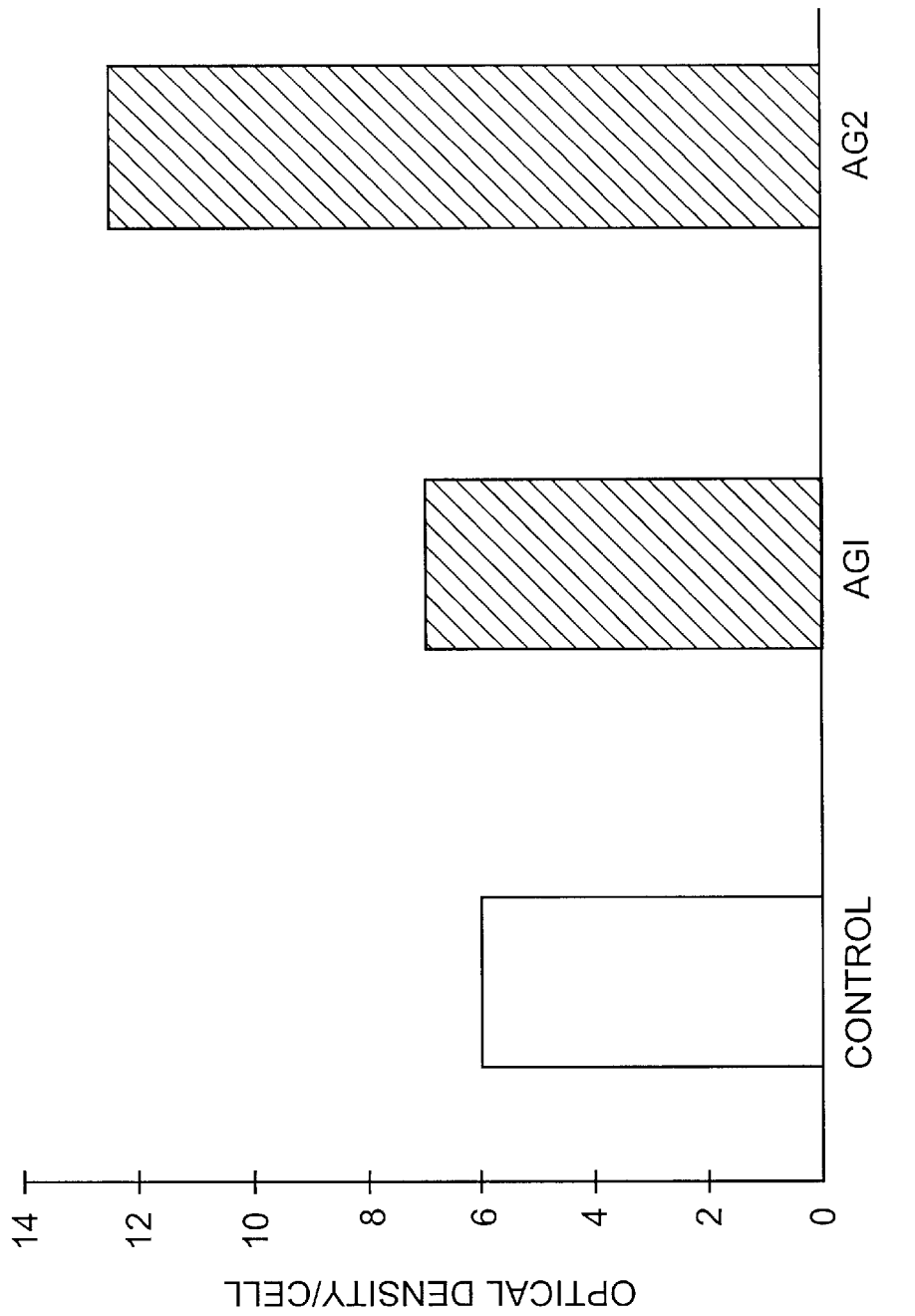
FIG. 3 Represents a graph illustrating effects of AG on mitochondrial activity in neuroblastoma cells.
Figure 4:
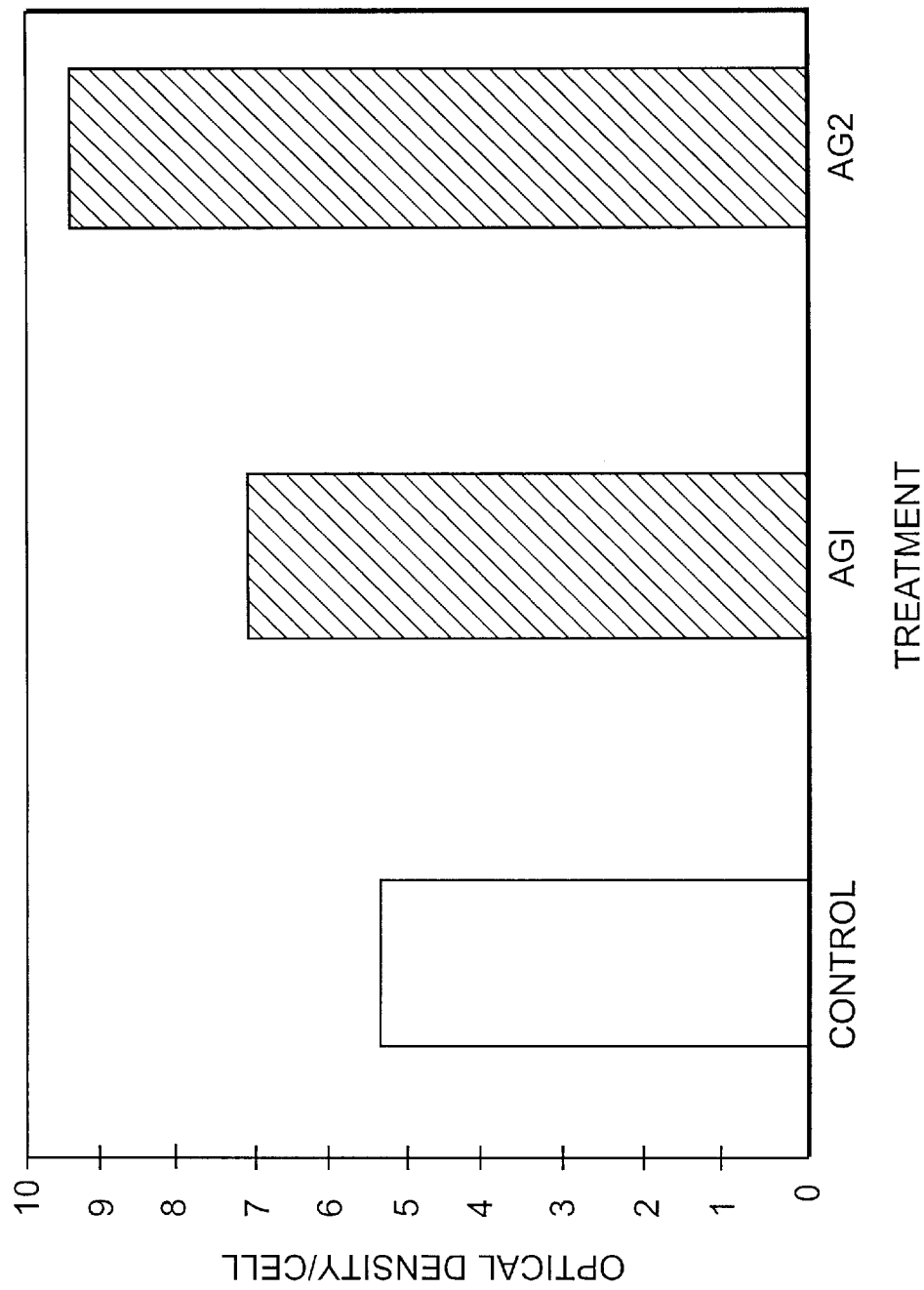
FIG. 4 Represents a graph illustrating effects of AG on reactive oxygen species in neuroblastoma cells FIG. 5 Represents a graph illustrating effects of AG on neuroblastoma cells FIG. 6 Represents a graph illustrating effects of AG on the level of UCP-protein in neuroblastoma cells

Further experiments have shown that aminoguanidine carboxylic acid (AG) increase mitochondrial activity (FIG. 3) and the generation of reactive oxygen species (ROS) (FIG. 4) in human neuroblasloma cells treated for 2 days.

EXAMPLE 3

Microcalorimetry.

Figure 5:
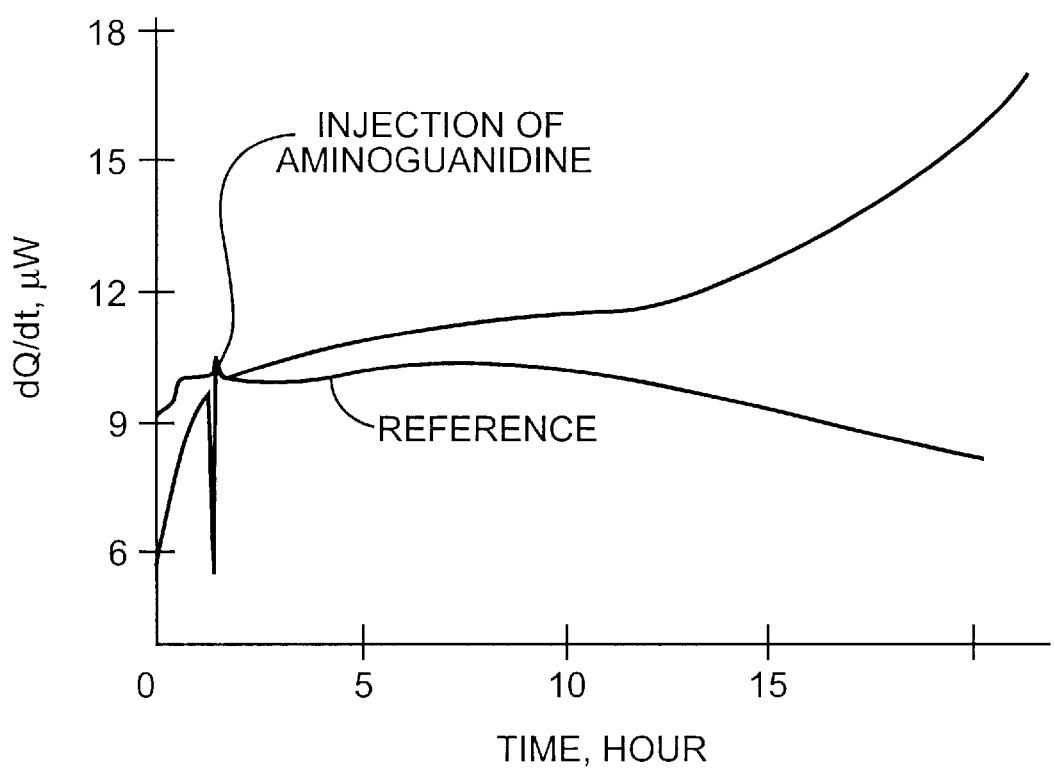

In SH-SY5Y cells, as well as in L6 (rat myocytes) cells AG has been shown, by microcalorimetry, to be thermogenic. The increase in heat production initiated by the AG required several hours of incubation to establish (FIG. 5).

EXAMPLE 4

Cytometer

L6 cells and SH-SY5Y cells were shown to express UCP2 on the mRNA-level as well as the protein level. Using a laser scanner cytometer it was possible to show a shift in the peak fluorescence of antibody labelled UCP2 protein in SH-SY5Y cells after AG treatment. Increases in the protein level of UCP2 in SH-SY5Y could be detected after treatment with AG by standard flow cytometry. (FIG. 6).

Conclusion

These data indicate the first example of a drug-induced upregulation of UCP-2 mRNA. Furthermore, we have found that, as a consequence of this, the level of UCP-2 protein increases and mitochondrial activity and heat flow increase. This serves as a foundation of an invention related to the drug-induced increase of metabolic efficiency, increase in energy expenditure, and increase thermogenesis by genetic or transcriptional upregulation of UCP-2 in adipose tissue. Drugs that increase energy expenditure are useful in the treatment of obesity, non-insulin dependent diabetes, as well as the metabolic syndrome.

contacting cells endogenously expressing UCP-2 with a potential drug for treating obesity, metabolic syndrome or non-insulin dependent diabetes mellitus;

cultivating the cells; and measuring in vitro at least one indicator related to UCP-2 production of the cells.

2. The method according to claim 1, wherein the indicator related to UCP-2 production includes at least one of level of upregulation of UCP-2 gene transcription and level of UCP-2 mRNA.

3. The method according to claim 1, wherein cultivating the cells includes culturing the cells in vitro.

4. The method according to claim 1, wherein contact of the cells with the potential drug is carried out in vivo.

5. The method according to claim 3, wherein the culture of cells includes 3T3-L1 cells or 3T3-F442A cells.

6. The method according to claim 5, wherein the cells have beein differentiated to adipocyte-like cells.

7. The method according to claim 3, wherein the cells have been derived from adipose tissue.

8. The method according to claim 4, wherein contact compris-es injecting the potential drug into a mouse.

9. The method according to claim 1, wherein the measurement is carried out by a method selected from the group consisting of biochemical, chemical, and physical methods.

10. The method according to claim 1, wherein the indicator of UCP-2 production also measures activity of a reporting gene.

We claim:

1. A method for screening for potential drugs for treating obesity, metabolic syndrome or non-insulin dependent diabetes mellitus, the method comprising the steps of:

11. The method according to claim 10, wherein the reporting gene is selected from the group consisting of *E. coli* β-galactosidase, chloramphenicol acetyltransferase, alkaline phosphatase, and firefly luciferase.

12. The method according to claim 1, wherein the indicator of UCP-2 production measures mitochondrial activity in the cells.

13. The method according to claim 1, wherein the indicator of UCP-2 production measures heat production in the cells.

14. A method for screening a potential regulator of UCP-2 transcription activity, the method comprising:

contacting a first group of cells with the potential regulator;

culturing the first group of cells;

measuring the level of UCP-2 transcription activity in the first group of cells;

contacting a second group of cells with a control substance;

culturing the second group of cells;

measuring the level of UCP-2 transcription activity in the second group of cells;

comparing the level of UCP-2 transcription activity in the first group of cells and the second group of cells; and selecting a potential regulator that causes an increased level of UCP-2 transcription activity in comparison to the level of UCP-2 transcription activity caused by the control substance.

15. The method according to claim 14, wherein measuring the level of UCP-2 transcription activity comprises measuring UCP-2 mRNA production.

16. The method according to claim 14, wherein cultivating the first group of cells and the second group of cells includes culturing the cells in vitro.

17. The method according to claim 14, wherein contact of the cells with the potential regulator is carried out in vivo.

18. The method according to claim 16, wherein the first group of cells and the second group of cells include 3T3-L1 cells or 3T3-F442A cells.

19. The method according to claim 18, wherein the cells have been differentiated to adipocyte-like cells.

20. The method according to claim 16, wherein the cells have been derived from adipose tissue.

21. The method according to claim 17, wherein contact comprises injecting the potential regulator into a mouse.

22. The method according to claim 14, wherein adipose cells and skeletal muscle cells are each contacted with the potential regulator and the control substance, the adipose cells and the skeletal muscle cells are cultured, the level of UCP-2 transcription activity in adipose cells and the skeletal cells are measured for the potential regulator and the control substance, the level of UCP-2 transcription activity the adipose cells and the skeletal muscle cells is measured, and a potential regulator is selected that causes an increased level of UCP-2 transcription activity in adipose cells as compared to skeletal muscle cells.

23. A method for determining upregulation of UCP-2 for identifying potential drugs for treating obesity, metabolic syndrome or non-insulin dependent diabetes mellitus, the method comprising:

contacting cells endogenously expressing UCP-2 with a potential drug for treating obesity, metabolic syndrome or non-insulin dependent diabetes mellitus;

cultivating the cells; and utilizing a cDNA probe to detect UCP-2 mRNA.

24. The method according to claim 23, wherein the cells comprise adipose tissue.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: both (ii) MOLECULE TYPE: other nucleic acid
      (A) DESCRIPTION: /desc = "artifical primer"

(xi) SEQUENCE DESCRIPTION: SEQ ID NO:1:

CCAGTCACGA CGTTGTAAA           19

(2) INFORMATION FOR SEQ ID NO:2:

(i) SEQUENCE CHARACTERISTICS:
      (A) LENGTH: 19 base pairs
      (B) TYPE: nucleic acid
      (C) STRANDEDNESS: single
      (D) TOPOLOGY: unknown (ii) MOLECULE TYPE: other nucleic acid
      (A) DESCRIPTION: /desc = "artifical primer"

(xi) SEQUENCE DESCRIPTION: SEQ ID NO:2:

CACAGGAAAC AGCTATGAC           19